United States Patent [19]

Matsuyama et al.

[11] Patent Number: 5,288,620
[45] Date of Patent: Feb. 22, 1994

[54] PROCESS FOR THE PRODUCTION OF OPTICALLY ACTIVE 2-HYDROXY-4-PHENYL-3-BUTENOIC ACID

[75] Inventors: Akinobu Matsuyama, Niigata; Ichiro Takase; Yoichiro Ueda, both of Hyogo; Yoshinori Kobayashi, Niigata, all of Japan

[73] Assignee: Daicel Chemical Industries, Ltd., Osaka, Japan

[21] Appl. No.: 885,974

[22] Filed: May 20, 1992

Related U.S. Application Data

[62] Division of Ser. No. 459,787, Mar. 1, 1990, Pat. No. 5,194,380.

[30] Foreign Application Priority Data

Jul. 12, 1988 [JP] Japan .................. 63-173464
Jul. 12, 1988 [JP] Japan .................. 63-173470
Oct. 7, 1988 [JP] Japan .................. 63-253020

[51] Int. Cl.$^5$ .................. C12P 7/42; C12R 1/22; C12R 1/01; C12R 1/645

[52] U.S. Cl. .................. 435/146; 435/280; 435/822; 435/824; 435/830; 435/836; 435/840; 435/843; 435/850; 435/852; 435/853; 435/857; 435/873; 435/874; 435/885; 435/911; 435/921; 435/930

[58] Field of Search .............. 435/146, 280, 822, 824, 435/830, 836, 840, 843, 850, 852, 853, 857, 873, 874, 885, 911, 921, 930

[56] References Cited

FOREIGN PATENT DOCUMENTS 6187640 10/1984 Japan .

OTHER PUBLICATIONS

Nerdel et al., (1956), Chem. Ber., 89:671–677.

*Primary Examiner*—Herbert J. Lilling
*Attorney, Agent, or Firm*—Birch, Stewart, Kolasch & Birch

[57] ABSTRACT

Optically active 2-hydroxy-4-phenyl-3-butenoic acid can be obtained by treating 2-oxo-4-phenyl-3-butenoic acid with an optionally treated microorganism capable of asymmetrically reducing the 2-oxo-4-phenyl-3-butenoic acid into (R)-2-hydroxy-4-phenyl-3-butenoic acid or (S)-2-hydroxy-4-phenyl-3-butenoic acid to thereby asymmetrically reduce the same into (R)-2-hydroxy-4-phenyl-3-butenoic acid or (S)-2-hydroxy-4-phenyl-3-butenoic acid.

2 Claims, No Drawings

PROCESS FOR THE PRODUCTION OF OPTICALLY ACTIVE 2-HYDROXY-4-PHENYL-3-BUTENOIC ACID

This application is a divisional of copending application Ser. No. 07/459,787, filed on Mar. 1, 1990 now U.S. Pat. No. 5,194,380, the entire contents of which are hereby incorporated by reference.

BACKGROUND OF THE INVENTION

This invention relates to a process for the production of optically active 2-hydroxy-4-phenyl-3-butenoic acid. More particularly, it relates to a process for the production of optically active 2-hydroxy-4-phenyl-3-butenoic acid which comprises treating 2-oxo-4-phenyl-3-butenoic acid with an optionally treated microorganism capable of asymmetrically reducing the 2-oxo-4-phenyl-3-butenoic acid into (R)-2-hydroxy-4-phenyl-3-butenoic acid or (S)-2-hydroxy-4-phenyl-3-butenoic acid, and collecting the (R)-2-hydroxy-4-phenyl-3-butenoic acid or (S)-2-hydroxy-4-phenyl-3-butenoic acid thus formed.

Optically active 2-hydroxy-4-phenyl-3-butenoic acid is an important intermediate in the production of various drugs, optically active and physiologically active substances, and derivatives thereof.

Further, optically active 2-hydroxy-4-phenyl-butyric acid, which is an important intermediate in the production of drugs such as ACE inhibitors, can be readily obtained by bringing optically active 2-hydroxy-4-phenyl-3-butenoic acid into contact with a hydrogenation catalyst such as palladium in a hydrogen atmosphere.

PRIOR ART

Known methods for the production of optically active 2-hydroxy-4-phenyl-3-butenoic acid include one which comprises treating a racemic mixture of said acid with bornylamine to thereby form diastereomers and then optically resolving the same [cf. Chem. Ber., 89, 671-677 (1956)], and another one comprising optical resolution through liquid chromatography with the use of a packing comprising a carrier containing a metal salt of an optically active amino acid bound thereto (cf. Japanese Patent Laid-Open No. 87640/1986). However, the former method requires a complicated procedure, which makes it undesirable from an industrial viewpoint. On the other hand, the latter method is disadvantageous from an economic viewpoint. Thus, it has been necessary to develop a simple and economical method therefor. In addition, no process has been described for the production of optically active 2-hydroxy-4-phenyl-3-butenoic acid from 2-oxo-4-phenyl-3-butenoic acid by using a microorganism capable of asymmetrically reducing the 2-oxo-4-phenyl-3-butenoic acid.

Disclosure of the Invention

The present inventors have developed asymmetric reduction with a microorganism as a process for readily producing optically active 2-hydroxy-4-phenyl-3-butenoic acid of high optical purity and attempted to discover microorganisms suitable for this purpose. As a result, they have determined that a microorganism belonging to the genus Lactobacillus, Leuconostoc, Streptococcus, Sporolactobacillus, Pediococcus, Arthrobacter, Agrobacterium, Ambrosiozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella or Xanthomonas can asymmetrically reduce 2-oxo-4-phenyl-3-butenoic acid to thereby give (R)-2-hydroxy-4-phenyl-3-butenoic acid, and that a microorganism belonging to the genus Lactobacillus, Leuconostoc or Streptococcus can asymmetrically reduce 2-oxo-4-phenyl-3-butenoic acid to thereby give (S)-2-hydroxy-4-phenyl-3-butenoic acid, thus completing the present invention.

In the present invention, therefore, any microorganism belonging to the genus Lactobacillus, Leuconostoc, Streptococcus, Sporolactobacillus, Pediococcus, Arthrobacter, Agrobacterium, Ambrosiozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella or Xanthomonas and capable of asymmetrically reducing 2-oxo-4-phenyl-3-butenoic acid to thereby give (R)-2-hydroxy-4-phenyl-3-butenoic acid or any one belonging to the genus Lactobacillus, Leuconostoc. or Streptococcus and capable of asymmetrically reducing 2-oxo-4-phenyl-3-butenoic acid to thereby give (S)-2-hydroxy-4-phenyl-3-butenoic acid can be used.

Particular examples of a microorganism capable of producing (R)-2-hydroxy-4-phenyl-3-butenoic acid from 2-oxo-4-phenyl-3-butenoic acid include *Lactobacillus lactis* AHU 1059, *Streptococcus faecalis* IFO 12964, *Leuconostoc mesenteroides* subsp. *dextranicum* IFO 3349, *Pediococcus acidilactici* NRIC 1102, *Sporolactobacillus inulinus* NRIC 1133, *Arthrobacter citreus* IAM 12341, *Agrobacterium radiobacter* IFO 12664, *Ambrosiozyma cicatricosa* IFO 1846, *Ambrosiozyma platypodis* IFO 1471, *Achromobacter pestifer* ATCC 23584, *Arthroascus javanensis* IFO 1848, *Aureobacterium testaceum* IFO 12675, *Bacillus licheniformis* IFO 12200, *Botryoascus synnaedendrus* IFO 1604, *Brevibacterium iodinum* IFO 3558, *Candida parapsilosis* IFO 1396, *Candida rugosa* IFO 0750, *Clavispora lusitaniae* IFO 1019, *Corynebacterium glutanicum* ATCC 13032, *Flavobacterium suaveolens* IFO 3752, *Geotrichum candidum* IFO 4601, *Hansenula fabianii* IFO 1253, *Kluyveromyces lactis* IFO 1903, *Lipomyces starkeyi* IFO 1289, *Lodderomyces elongisporus* IFO 1676, *Proteus vulgaris* IFO 3167, *Pseudomonas aureotaciens* IFO 3522, *Saccharomycopsis lipolytica* IFO 1550, *Saccharomycopsis fibuligera* IFO 0103, *Schizosaccharomyces octosporus* IFO 0353, *Stephanoascus ciferrii* IFO 1854, *Torulaspora delbrueckii* IFO 0381, *Trigonopsis variabillis* IFO 0755, *Wickerhamiella domercquii* IFO 1857, *Enterobacter aerogenes* AHU 1338, *Klebsiella pneumoniae* IAM 1063 and *Xanthomonas oryzae* IAM 1657.

On the other hand, examples of a microorganism capable of producing (S)-2-hydroxy-4-phenyl-3-butenoic acid from 2-oxo-4-phenyl-3-butenoic acid include *Lactobacillus plantrum* IFO 3070, *Streptococcus lactis* NRIC 1149 and *Leuconostoc mesenteroides* AHU 1416.

These microorganisms may be either wild strains, variants, or recombinants obtained through genetic engineering techniques such as cell fusion or gene manipulation.

The microorganisms having IFO numbers assigned thereto are described in the List of Cultures, 8th ed., vol. 1 (1988) published by the Institute for Fermentation, Osaka (IFO) and are available therefrom. Those having AHU numbers are described in the Catalogue of Cultures, 4th ed. (1987) published by Japan Federation of Culture Collection (JFCC) and are available from the Faculty of Agriculture, Hokkaido University. Further, those having ATCC numbers are described in the Catalogue of Bacteria Phages rDNA Vectors, 16th ed. (1985) published by American Type Culture Collection (ATCC) and are available therefrom. Those having NRIC numbers are described in the Culture Collection of NODAI No. 1 (1985) published by Tokyo University of Agriculture and are available therefrom. Those having IAM numbers are available form the Institute of Applied Microbiology, the University of Tokyo.

In order to culture the microorganism to be used in the present invention, any medium may be used without restriction, so long as said microorganism can grow therein. For example, any carbon source available for said microorganism may be used. Examples thereof include sugars such as glucose, fructose, sucrose and dextrin; alcohols such as sorbitol, ethanol and glycerol; organic acids such as fumaric acid, citric acid, acetic acid and propionic acid and salts thereof; hydrocarbons such as paraffin, and mixtures thereof. Examples of a nitrogen source include ammonium salts of inorganic acids, such as ammonium chloride, ammonium sulfate and ammonium phosphate; ammonium salts of organic acids, such as ammonium fumarate and ammonium citrate; organic or inorganic nitrogen-containing compounds such as meat extract, yeast extract, corn steep liquor, casein hydrolyzate and urea; and mixtures thereof. The medium may further contain appropriate nutritional sources commonly employed in culturing microorganisms, for example, inorganic salts, trace metal salts and vitamins. Furthermore, a growth promoter for the microorganism, a factor capable of elevating the productivity of the target compound of the present invention, or a substance effective in maintaining the pH value of the medium at a desired level may be added thereto.

The culture may be conducted at a pH value of from 3.5 to 9.5, preferably from 4 to 8, at a temperature of from 20° to 45° C., preferably from 25° to 37° C., under aerobic or anaerobic conditions suitable for each microorganism for from 5 to 120 hours, preferably from 12 to 72 hours.

The reduction may be conducted by using the culture medium as such. Alternately, the cells may be separated by, for example, centrifuging, and optionally washed. Then the cells are resuspended in a buffer solution or water, and 2-oxo-4-phenyl-3-butenoic acid is added to the suspension thus obtained and reacted therewith. In this reaction, it is sometimes preferable to add a carbon source such as glucose or sucrose to thereby supply energy. The cells may be used as such in the form of viable cells. Alternately, they may be those which have been ground, treated with acetone or lyophilized. These optionally treated cells may be immobilized prior to the use by a conventional method, for example, the polyacrylamide gel method, the sulfur-containing polysaccharide gel method (the carrageenan gel method), the alginic acid gel method or the agar gel method. Furthermore, an enzyme obtained from said treated cells by combining known methods may be used therefor.

The 2-oxo-4-phenyl-3-butenoic acid may be used as such. Alternately, it may be dissolved in water or an inert organic solvent, or dispersed in a surfactant. It may be added either at once at the initiation of the reaction, or in portions. The 2-oxo-4-phenyl-3-butenoic acid may be used in the form of various salts such as ammonium, sodium, calcium or potassium salts.

The reaction may be conducted at a pH value of from 3 to 9, preferably from 5 to 8, at from 10° to 60° C., preferably from 20° to 40° C., for from 1 to 120 hours with or without stirring. It is preferable that the concentration of the substrate ranges from 0.1 to 10%, though it is not restricted thereby.

The optically active 2-hydroxy-4-phenyl-3-butenoic acid thus formed may be collected directly from the reaction mixture or after separating the cells. It may be extracted with an organic solvent and then purified by a common method such as column chromatography or recrystallization.

According to the process of the present invention for the production of optically active 2-hydroxy-4-phenyl-3-butenoic acid by using a microorganism, optically active 2-hydroxy-4-phenyl-3-butenoic acid of a high optical purity can be readily produced. Thus it is highly advantageous as an industrial process.

EXAMPLES

To further illustrate the present invention, and not by way of limitation, the following Examples will be given.

In the following Examples, the absolute configuration and optical purity of the reaction product were determined by extracting the reaction product with ethyl acetate and subjecting the product to high-performance liquid chromatography with the use. of an optical resolution column [column: Chiral-pack WH (mfd. by Daicel Chemical Industries, Ltd., packed with silica gel containing copper salt of L-proline bound thereto), 4.6 mm (i.d.)×250 mm, solvent: 0.5 mM $CuSO_4$/acetonitrile=4:1, flow rate: 1.5 ml/min, detection: at 254 nm]. The reaction yield was determined by high-performance liquid chromatography with the use of a reverse-phase column [column: Nucleosil 10C18, 4.6 mm (i.d.)×250 mm, solvent: 40 mM potassium phosphate solution (pH 3.0)/acetonitrile=4:1, flow rate: 1 ml/min, detection: at 254 nm].

Example 1

A medium comprising 2% of glucose, 1% of yeast extract, 1% of peptone, 10 ppm of $MnSO_4$ and 1% of calcium carbonate was used for lactic acid bacteria; a medium comprising 1% of glucose, 0.5% of yeast extract, 0.5% of peptone, 0.5% of meat extract and 0.5% of NaCl (pH 7) was used for other bacteria; and a medium comprising 2% of glucose, 0.3% of yeast extract, 0.5% of peptone and 0.3% of malt extract (pH 6) was used for yeasts. 100 ml of each medium was introduced into a 500-ml Erlenmeyer flask and sterilized. Then one platinum loopful, of each strain listed in Table 1 was inoculated into the corresponding medium and subjected to rotary shaking culture for 48 hours. After the completion of the culture, the cells were separated by centrifuging and washed with a physiological saline solution once to thereby yield viable cells. 50 ml of distilled water was introduced into a 500-ml Erlenmeyer flask and the above-mentioned viable cells were suspended therein. After adding 5 g of sucrose and 0.5 g of calcium carbonate thereto, the mixture was shaken at 30° C. for 10 minutes. Then 0.5 g of potassium 2-keto-4- phenyl-3-butenoate was added thereto and the mixture was allowed to react under shaking at 30° C. for 40 hours. After the completion of the reaction, the pH value of the reaction mixture was adjusted to 1 or below with sulfuric acid. It was then extracted with 100 ml of ethyl acetate, and the solvent was removed from the extract. Then the amount and optical purity of the (R)-2-hydroxy-4-phenyl-3-butenoic acid thus formed were determined by high-performance liquid chromatography.

Table 1 summarizes the results.

TABLE 1

| Strain | Yield of (R)-2-hydroxy-4-phenyl-3-butenoic acid (%) | Optical purity of (R)-2-hydroxy-4-phenyl-3-butenoic acid (% e.e.) |
|---|---|---|
| Lactobacillus lactis AHU 1059 | 11 | 67 |
| Streptococcus faecalis IFO 12964 | 14 | 62 |
| Leuconostoc mesenteroides subsp. dextranicum IFO 3349 | 92 | 100 |
| Pediococcus acidilactici NRIC 1102 | 10 | 100 |
| Sporolactobacillus inulinus NRIC 1133 | 16 | 68 |
| Lactobacillus lactis ATCC 12315 | 16 | 100 |
| Lactobacillus viridescens ATCC 12706 | 14 | 46 |
| Leuconostoc dextranicum ATCC 17072 | 96 | 100 |
| Leuconostoc mesenteroides AHU 1067 | 93 | 100 |
| Arthrobacter citreus IAM 12341 | 20 | 100 |
| Agrobacterium radiobacter IFO 12664 | 13 | 100 |
| Ambrosiozyma cicatricosa IFO 1846 | 11 | 100 |
| Ambrosiozyma platypodis IFO 1471 | 10 | 100 |
| Achromobacter pestifer ATCC 23584 | 15 | 100 |
| Arthroascus javanensis IFO 1848 | 12 | 32 |
| Aureobacterium testaceum IFO 12675 | 12 | 20 |
| Bacillus licheniformis IFO 12200 | 10 | 100 |
| Botryoascus synnaedendrus IFO 1604 | 13 | 100 |
| Brevibacterium iodinum IFO 3558 | 15 | 100 |
| Candida parapsilosis IFO 1396 | 19 | 100 |
| Saccharomycopsis lipolytica IFO 1550 | 12 | 100 |
| Saccharomycopsis fibuligera IFO 0103 | 13 | 100 |
| Schizosaccharomyes octosporus IFO 0353 | 10 | 100 |
| Stephanoascus ciferrii IFO 1854 | 19 | 100 |
| Torulaspora delbrueckii IFO 0381 | 14 | 100 |
| Trigonopsis variabillis IFO 0755 | 15 | 100 |
| Wickerhamiella domercquii IFO 1857 | 11 | 95 |
| Enterobacter aerogenes AHU 1338 | 13 | 94 |
| Klebsiella pneumoniae IAM 1063 | 12 | 70 |
| Xanthomonas oryzae AIM 1657 | 11 | 100 |
| Lactobacillus plantrum IFO 3070 | 24 | 99 |
| Streptococcus lactis NRIC 1149 | 32 | 49 |

TABLE 1-continued

| Strain | Yield of (R)-2-hydroxy-4-phenyl-3-butenoic acid (%) | Optical purity of (R)-2-hydroxy-4-phenyl-3-butenoic acid (% e.e.) |
|---|---|---|
| Leuconostoc mesenteroides AHU 1416 | 14 | 100 |
| Candida rugosa IFO 0750 | 17 | 100 |
| Calvispora lusitaniae IFO 1019 | 16 | 100 |
| Corynebacterium glutamicum ATCC 13032 | 11 | 93 |
| Flavobacterium suaveolens IFO 3752 | 11 | 70 |
| Geotrichum candidum IFO 4601 | 19 | 100 |
| Hansenula fabianii IFO 1253 | 13 | 100 |
| Kluyveromyces lactis IFO 1903 | 14 | 100 |
| Lipomyces starkeyi IFO 1289 | 10 | 83 |
| Lodderomyces elongisporus IFO 1676 | 14 | 100 |
| Proteus vulgaris IFO 3167 | 10 | 100 |
| Pseudomonas aureotaciens IFO 3522 | 11 | 100 |

Example 2

2 l of the same medium as that used in Example 1 contained in a 5-l jar fermenter was inoculated with Leuconostoc mesenteroides subsp. dextranicum IFO 3349. The strain was cultured at 30° C. under stirring at 100 rpm for 40 hours. After the completion of the culture, the cells were collected by centrifuging and washed with 1 l of water. Then these cells were suspended in 500 ml of water, and 5 g of potassium 2-keto-4-phenyl-3-butenoate, 50 g of glucose and 4 g of calcium carbonate were added thereto. The obtained mixture was allowed to react at 30° C. under stirring for 48 hours and then the pH value thereof was adjusted to 1 or below with sulfuric acid. Then it was extracted with the same amount of ethyl acetate twice. The ethyl acetate phase was dehydrated over anhydrous Galuber's salt and the solvent was removed therefrom under reduced pressure. Thus 4.0 g of 2-hydroxy-4-phenyl-3-butenoic acid were obtained in the form of crude crystals. By recrystallizing from ethanol, 3.8 g of crystals of (R)-2-hydroxy-4-phenyl-3-butenoic acid were obtained (optical purity: 100% e.e., yield: 93%).

What is claimed is:

1. A process for the production of optically active 2-hydroxy-4-phenyl-3-butenoic acid, which comprises:
    treating a microorganism selected from the group of genera consisting of Lactobacillus, Leuconostoc, Streptococcus, Sporolactobacillus, Pediococcus, Arthrobacter, Agrobacterium, Ambrosiozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella and Xanthomonas by a treatment selected from the group consisting of grinding, treating with acetone and lyophilizing, to obtain an enzyme preparation having the biochemical activity of reducing 2-oxo-4-phenyl-3-butenoic acid to form (S)-2-hydroxy-4-phenyl-3-butenoic acid or (R)-2-hydroxy-4-phenyl-3 butenoic acid; and
    treating 2-oxo-4-phenyl-3-butenoic acid with said enzyme preparation.

2. A process as recited in claim 1, wherein said enzyme preparation is immobilized.

* * * * *